(12) United States Patent
Savitsky et al.

(10) Patent No.: US 11,062,624 B2
(45) Date of Patent: *Jul. 13, 2021

(54) EMBEDDED MOTION SENSING TECHNOLOGY FOR INTEGRATION WITHIN COMMERCIAL ULTRASOUND PROBES

(71) Applicant: SonoSim, Inc., Santa Monica, CA (US)

(72) Inventors: Eric Savitsky, Malibu, CA (US); Dan Katz, Encino, CA (US); Gabriele Nataneli, Beverly Hills, CA (US)

(73) Assignee: THE REGENTS OF UNIVERSITY OF CALIFORNIA, Oakland, CA (US)

( * ) Notice: Subject to any disclaimer, the term of this patent is extended or adjusted under 35 U.S.C. 154(b) by 419 days.

This patent is subject to a terminal disclaimer.

(21) Appl. No.: 16/037,796

(22) Filed: Jul. 17, 2018

(65) Prior Publication Data
US 2018/0330635 A1    Nov. 15, 2018

Related U.S. Application Data

(63) Continuation of application No. 13/481,725, filed on May 25, 2012, now Pat. No. 10,026,338, which is a continuation-in-part of application No. 13/243,758, filed on Sep. 23, 2011, now Pat. No. 8,480,404, which is a continuation of application No. 11/720,515, filed
(Continued)

(51) Int. Cl.
*G09B 23/28* (2006.01)
*A61B 8/00* (2006.01)

(52) U.S. Cl.
CPC .......... *G09B 23/286* (2013.01); *A61B 8/4254* (2013.01)

(58) Field of Classification Search
CPC ............................ G09B 23/286; A61B 8/4254
See application file for complete search history.

(56) References Cited

U.S. PATENT DOCUMENTS

| 5,513,992 | A | 5/1996 | Refait |
| 5,609,485 | A | 3/1997 | Bergman et al. |
| 5,701,900 | A | 12/1997 | Shehada et al. |

(Continued)

FOREIGN PATENT DOCUMENTS

WO    2006060406    6/2006

OTHER PUBLICATIONS

Simulab Corporation, "TraumaMan [registered] System," www.simulab.comffraumaSurgery.htm, 3 pgs, obtained from website Dec. 7, 2004.
(Continued)

*Primary Examiner* — Amelie R Davis
*Assistant Examiner* — John Denny Li
(74) *Attorney, Agent, or Firm* — Cislo & Thomas, LLP

(57) ABSTRACT

An ultrasound system including an ultrasound machine and an ultrasound probe. The ultrasound probe includes an ultrasound transducer, ultrasound circuitry, a six degree of freedom (6-DOF) sensor, and a probe housing. The probe housing encases the ultrasound transducer and the 6-DOF sensor. By embedding motion-sensing technology directly within the housing of the ultrasound transducer, the position and orientation of the ultrasound probe can be tracked in an automated manner in relation to an indicator mark on the ultrasound screen. This allows assisting technologies to mitigate human error that arises from misalignment of the transducer indicator.

20 Claims, 4 Drawing Sheets

Related U.S. Application Data as application No. PCT/US2005/043155 on Nov. 30, 2005, now abandoned.

(60) Provisional application No. 60/631,488, filed on Nov. 30, 2004, provisional application No. 61/491,126, filed on May 27, 2011, provisional application No. 61/491,131, filed on May 27, 2011, provisional application No. 61/491,134, filed on May 27, 2011, provisional application No. 61/491,135, filed on May 27, 2011, provisional application No. 61/491,138, filed on May 27, 2011.

(56) References Cited

U.S. PATENT DOCUMENTS

| | | |
|---|---|---|
| 5,704,791 A | 1/1998 | Gillio |
| 5,755,577 A | 5/1998 | Gillio |
| 5,767,839 A | 6/1998 | Rosenberg |
| 5,776,062 A | 7/1998 | Nields |
| 5,791,908 A | 8/1998 | Gillio |
| 5,800,177 A | 9/1998 | Gillio |
| 5,800,178 A | 9/1998 | Gillio |
| 5,800,179 A | 9/1998 | Bailey |
| 5,800,350 A | 9/1998 | Coppleson et al. |
| 5,882,206 A | 3/1999 | Gillio |
| 6,068,597 A | 5/2000 | Lin |
| 6,074,213 A | 6/2000 | Hon |
| 6,113,395 A | 9/2000 | Hon |
| 6,117,078 A | 9/2000 | Lysyansky et al. |
| 6,122,538 A | 9/2000 | Sliwa, Jr. et al. |
| 6,156,213 A | 12/2000 | Dudley et al. |
| 6,267,599 B1 | 7/2001 | Bailey |
| 6,511,427 B1 | 1/2003 | Sliwa, Jr. et al. |
| 6,654,000 B2 | 11/2003 | Rosenberg |
| 6,693,626 B1 | 2/2004 | Rosenberg |
| 6,694,163 B1 | 2/2004 | Vining |
| 6,714,213 B1 | 3/2004 | Lithicum et al. |
| 6,714,901 B1 | 3/2004 | Cotin et al. |
| 6,750,877 B2 | 6/2004 | Rosenberg et al. |
| 6,780,016 B1 | 8/2004 | Toly |
| 6,816,148 B2 | 11/2004 | Mallett et al. |
| 6,896,650 B2 | 5/2005 | Tracey et al. |
| 6,916,283 B2 | 7/2005 | Tracey et al. |
| 7,037,258 B2 | 5/2006 | Chatenever et al. |
| 7,371,068 B2 | 5/2008 | Lloyd et al. |
| 7,794,388 B2 | 9/2010 | Draxinger et al. |
| 7,850,454 B2 | 12/2010 | Toly |
| 7,857,626 B2 | 12/2010 | Toly |
| 2001/0031920 A1 | 10/2001 | Kaufman et al. |
| 2002/0099310 A1 | 7/2002 | Kimchy et al. |
| 2002/0168618 A1 | 11/2002 | Anderson et al. |
| 2004/0043368 A1 | 3/2004 | Hsieh et al. |
| 2004/0087850 A1 | 5/2004 | Okerlund et al. |
| 2005/0119569 A1 | 6/2005 | Ohtake |
| 2005/0181342 A1 | 8/2005 | Toly |
| 2005/0283075 A1 | 12/2005 | Ma et al. |
| 2007/0232907 A1 | 10/2007 | Pelissier et al. |
| 2008/0204004 A1 | 8/2008 | Anderson |
| 2008/0269606 A1 | 10/2008 | Matsumura |
| 2010/0055657 A1 | 3/2010 | Goble et al. |

OTHER PUBLICATIONS

Small, S. D., "Medical education: thoughts on patient safety education and the role of simulations," Mar. 2004, http://virtualmentor.ama-assn.org/2004/03/medul-0403.html, Virtual Mentor, Mar. 2004, 6(3), 3 pgs, obtained from website Jan. 21, 2008.

Stanfield, S. et. al., "Design and implementation of a virtual reality system and its application to training medical first responders," Presence, 9(6), (2000) pp. 524-556.

Steele, R., and Irwin, C. B., "Central line mechanical complication rate in emergency medicine patients," Acad Emerg Med, 2001, 8(2):204-207, 8 pgs, obtained from website Sep. 8, 2004.

Summit, Stanford University Medical Media & Information Technologists, corporate home page directory and information regarding simulators in immersive learning environments, 6 pgs, obtained from website Dec. 7, 2004.

Summit, "Gaming and simulation based learning: applications for medicine,", SIM workshops, Jan. 25, 2005, http://summit.stanford.edu, 3 pgs, obtained from website Dec. 7, 2004.

Summit, "Virtual 3D world for emergency medical team training," http://summit.stanford.edu/research/simtech_project. html, 2 pgs, obtained from website Dec. 7, 2004.

Summit, "Simulation environments in medicine," http://summit.stanford.edu/research/simulationevironinmed_project.html, 1 pg, obtained from website Dec. 7, 2004.

Texas Heart Institute, "First medical simulation training center in southern U.S. opening at Texas Heart Institute and St. Luke's Episcopal Hospital," media advisory open house, 2 pgs, Oct. 1, 2003.

UCSD, "What is anatomic visualizeR [copyright] ?!lessons/3D models," http://meded.ucsd.edu/edcom/vr/anatvr.html, 5 pgs, obtained from website Sep. 6, 2004.

Van Beek, E. J. R., "Routine chest radiographs following central line insertion," CHEST J, www.chestjournal.org/cgi/contenUfull/127/1/10, 127(1):10—Chest, 3 pgs, obtained from website May 11, 2005.

Verefi Technologies, Inc, "Surgical simulators that work!," www.verefi.com/indexb.html, 1 pg, obtained from website Dec. 7, 2004.

Verefi Technologies, Inc, "Endotower [trademark]—The world's first fully functional endoscope navigation surgical simulator," www.verefi.com/endotower.html, 2 pgs, obtained from website Dec. 7, 2004.

Verplaetse, C., "Inertial proprioceptive devices: self-motion-sensing toys and tools," IBM SYST J, 1996; 35 (3&4):639-50.

Virtual Reality and Education Laboratory, "Other virtual reality and education web sites (non-vrel)," corporate home page regarding site guides, conferences, symposiums, 14 pgs, obtained from website Jan. 8, 2005.

Virtusmed, "Explore the virtual patienUimproved human-computer interaction for medical imaging," www.virtusmed.com, 2 pgs.

Volume Interactions, "The dextroscope [registered]," www.volumeinteractions.com/technology_rationale.html, 2 pgs, obtained from website Dec. 7, 2004.

Vozenilek, J. et. al., "See one, do one, teach one: advanced technology in medical education," Acad Emerg Med, Nov. 2004, 11(11):1149-1154.

Wang, H. E. et. al., "Multivariate predictors of failed prehospital endotracheal intubation," www.aemj.org/cgi/contenUfull/10/7/717, Acad Emerg Med, 12 pgs, obtained from website Sep. 8, 2004.

Wong, K. and Stewart, F., "Competency-based training of basic trainees using human cadavers," NCBI, Nat Lib of 20 Med, ANZ J Surg, Aug. 2004; 74(8):639-42; www.ncbi..nlm.nih.gov/entrez/, 1 pg, obtained from website Sep. 8, 2004 (abstract).

You, S. et. al., "Hybrid inertial and vision tracking for augmented reality registration," Virtual Reality, Mar. 1999; 13 (17):260-67.

Aligned Management Associates, Inc., Corporate home page describing organizing committee, overview, Procedicus MIST[trademark]-suturing module 30.0, 6 pgs., obtained from website Sep. 6, 2004.

American Academy of Emergency Medicine, conference: 11th annual scientific assembly preconference ultrasound courts, http://www. aaem.org/education/scientificassembly/sa05/precon/ultrasound.shtml, 6 pgs, obtained from website Feb. 16, 2005.

Barbosa, J. et. al., "Computer education in emergency medicine residency programs," http://www.med-ed-online.org/res00002.htm, 8 pgs, obtained from website Sep. 6, 2004.

Brannam, Let al, "Emergency nurses' utilization of ultrasound guidance for placement of peripheral intravenous lines in difficult-access patients," Acad Emerg Med, 11(12):1361-1363, Dec. 2004.

Calvert, N. et al., "The effectiveness and cost-effectiveness of ultrasound locating devices for central venous access: a systematic review and economic evaluation/executive summary," Health Tech Assess 2003, 7(12), 4 pgs.

Center for Human Simulation, corporate home page describing overview/people, http://www.uchsc.edu, 7 pgs, obtained from website Sep. 6, 2004.

(56) References Cited

OTHER PUBLICATIONS

Cimit News, "The medical access program: new CIMIT initiative to benefit underserved patients/partners telemedicine and CIMIT launch new initiative: stay connected, be healthy/highlights: operating room of the future plug-and-play project," http://www.cimit.org, Jan. 2005; vol. 2, 2 pgs., obtained from website Mar. 1, 2005.

Colt, H. G. et. al., "Virtual reality bronchoscopy simulation: a revolution in procedural training," Chest 2001; 120:1333-1339.

Computer Motion, "About computer motion: technology to enhance surgeons' capabilities, improve patient outcomes and reduce healthcare costs/corporate alliances/products & solutions for surgical innovation/training on the da Vinci[registered] surgical system-introduction," 2002 Computer Motion, http://www.computermotion.com, 6 pgs.

Delp, Setal, "Surgical simulation—an emerging technology for training in emergency medicine," Presence, 6(2):147-159, Apr. 1997 (abstract).

Dorner, R. et. al., "Synergies between interactive training simulations and digital storytelling: a component-based framework," Computer & Graphics, 26(1):45-55, Feb. 2002 (abstract).

Duque, D. and Kessler S., "Ultrasound guided vascular access," Amer Coli Emerg Phy., http://www.nyacep.org/education/articles/ultrasound%20vascular%20access.htm, 2 pgs, obtained from website May 11, 2005.

Espinet, A. and Dunning J., "Does ultrasound-guided central line insertion reduce complications and time to placement in elective patients undergoing cardiac surgery," Inter Cardiovascular Thoracic Surg, 3:523-527, 2004; http://licvts.ctsnetjournals.org/cgi/content/full/3/3/523, 6 pgs, obtained from website May 11, 2005 (abstract).

Gallagher, A. G. et al., "Virtual reality training for the operating room and cardiac catheterization laboratory," Lancet, 364:1538-1540, Oct. 23, 2004.

Gallagher, A. G. et. al., "Psychomotor skills assessment in practicing surgeons experienced in performing advanced laparoscopic procedures," AM Coli Surg, 197(3):479-488, Sep. 2003.

Gausche, M. et. al., "Effect on out-of-hospital pediatric endotracheal intubation on survival and neurological outcome: a controlled clinical trial," JAMA, 283(6):783-790, Feb. 9, 2000.

Gore, D. C. and Gregory, S. R., "Historical perspective on medical errors: Richard Cabot and the Institute of Medicine," J Amer Coli Surg, 197(4), 5 pgs, Oct. 2003.

Grantcharov, T. P. et. al., "Randomized clinical trial of virtual reality simulation for laparoscopic skills training," Br J Surg, 91(2):146-150, Feb. 1, 2004 (abstract).

Grantcharov, T. P. et. al., "Learning curves and impact of previous operative experience on performance on a virtual reality simulator to test laparoscopic surgical skills," Am J Surg, 185(2):146-149, Feb. 1, 2004 (abstract).

Haluck, R. S., et. al., "Are surgery training programs ready for virtual reality? A survey of program directors in general surgery," Arch Surg, 135(7):786-792, Jul. 1, 2000.

Helmreich, R. L., "On error management: lessons from aviation," BMJ, 320:781-785, Mar. 2000.

Huckman, R. S. and Pisano, G. P., "Turf battles in coronary revascularization," N Engl J Med, http://www.nejm.org, 4 pgs, 352(9):857-859, Mar. 3, 2005.

Immersion Corporation, URL: http://www.immersion.com/corporate/products/, corporate home page describing Immersion's surgical training simulators—"Wireless Data Glove: The CyberGiove[registered]ll System," 5 pgs, obtained from the website Nov. 17, 2005 and Jan. 24, 2008.

Injuryboard.com, "Reducing complications associated with central vein catheterization," URSL: http://www.injuryboard.com/view.cfm/Article=668, 5 pgs, obtained from website May 11, 2005.

Intersense, home page listing motion tracking products, http://www.isense.com/prodcuts.aspx?id=42&, 1 pg, obtained from website Jan. 24, 2008.

Jemmett, M. E., et. al., "Unrecognized misplacement of endotracheal tubes in a mixed urban to rural emergency medical services setting," Acad Emerg Med, 10(9):961-964, Sep. 2003.

Katz, S. H. and Falk, J. L., "Misplaced endotrachial tubes by paramedics in an urban medical services system," Annals Emerg Med, 37:32-37, Jan. 2001.

Lewis, R., "Educational research: time to reach the bar, not lower it," Acad Emerg Med, 12(3):247-248, Mar. 2005.

Liu, A. et. al., "A survey of surgical simulation: applications, technology, and education," Presence, 12(6):1-45, Dec. 2003.

Manchester Visulations Centre, "Webset project-bringing 3D medical training tools to the WWW," http://www.sve.man.ac.uklmvc/research/previous/website, 3 pgs, obtained from the website Sep. 8, 2004.

Mclellan, H., "Virtual realities," Mclellan Wyatt Digital, 33 pgs.

Medical Simulation Corporation, corporate home page describing management team/frequently asked questions, http://www.medsimulation.com/about_msc/key_employees.asp, 7 pgs, obtained from website Nov. 25, 2004.

Medtronic, "The StealthStation[registered] treatment guidance system," the corporate home page describing the company fact sheet and profile; http://www.medtronic.com/Newsroom, 4 pgs, obtained from website Mar. 5, 2005.

Mort, T. C., "Emergency tracheal intubation: complications associated with repeated laryngoscopic attempts," Anesth Analg, 99(2):607-613, Aug. 2004, 1 pg, obtained from website Sep. 8, 2004 (abstract).

Nazeer, S. R., et. al., "Ultrasound-assisted paracentesis performed by emergency physicians v.s. the traditional technique: a prospective, randomized study," Amer J of Emer Med, 23:363-367, 2005.

NCA Medical Simulation Center, Tutorial-simulation for medical training, http://Simcen.usuhs.millmiccaie, 4 pgs, 2003.

Next Dimension Imaging, "Products-Anatomy Analyzer 2," http://www.nexted.com/anatomyanalyzer.asp, 2 pgs, obtained from website Dec. 7, 2004.

Norris, T. E. et. al., "Teaching procedural skills," J General Internal Med, 12(S2):S64-S70, Apr. 1997.

On the Net Resources-Education and Training, URL: http://www.hitl.washington.edu/projects/knowledge_base/education.html, corporate home page regarding internet sites regarding education and training, 16 pgs, obtained from website Jan. 8, 2005.

Osberg, K. M., "Virtual reality and education: a look at both sides of the sword," http://www.hitl.washington.edu/publications/r-93-7/, 19 pgs, Dec. 14, 1992, obtained from website Jan. 21, 2008.

Osmon, S. et. al., "Clinical investigations: reporting of medical errors: an intensive care unit experience," Grit Care Med, 32(3), 13 pgs, Mar. 2004.

Ponder, M., et. al., "Immersive VR decision training: telling interactive stories featuring advanced human simulation technologies," Eurographics Association 2003, 10 pgs.

Primal, corporate home page describing resources for teaching healthcare practitioners, 2 pgs, obtained from website.

Prystowsky, J. B. et. al., "A virtual reality module for intravenous catheter placement," Am J Surg 1999; 177(2):171-175 (abstract).

Reachin, "Medical Training Development Centre/Reachin technologies AB has entered into a corporation with Mentice AB," Jan. 20, 2004, 4 pgs, obtained from website Nov. 9, 2004.

Rothschild, J. M., "Ultrasound guidance of central vein catheterization," NCBI, Nat Lib Med, www.ncbi.nlm.nih.gov/books/, HSTAT 21, 6 pgs, obtained from website May 11, 2005.

Rowe, R. and Cohen, R. A., "An evaluation of a virtual reality airway simulator," Anesth Analg 2002, 95:62-66.

Sensable Technologies, "PHANTOM Omni Haptic Device," 2 pgs, http://www.sensable.com/haptic-ohantom-omni.htm., obtained from website Jan. 24, 2008.

Shaffer, K., "Becoming a physician: teaching anatomy in a digital age," NEJM, Sep. 23, 2004; 351(13):1279-81 (extract of first 100 words -no abstract).

Simsuite, "Are you ready for your first carotid stent procedure/begin preparing now," www.simsuites.com/readarticle.asp?articleId=598, 1 pg, obtained from website Nov. 25, 2004.

EMBEDDED MOTION SENSING TECHNOLOGY FOR INTEGRATION WITHIN COMMERCIAL ULTRASOUND PROBES

CROSS-REFERENCES TO RELATED APPLICATIONS

This patent application is a continuation of U.S. patent application Ser. No. 13/481,725 filed May 25, 2012 for Embedded Motion Sensing Technology for Integration within Commercial Ultrasound Probes, which is a continuation-in-part of U.S. patent application Ser. No. 13/243,758 filed Sep. 23, 2011 for Multimodal Ultrasound Training System, which is a continuation of U.S. patent application Ser. No. 11/720,515 filed May 30, 2007 for Multimodal Medical Procedure Training System, which is the national stage entry of PCT/US05/43155, entitled "Multimodal Medical Procedure Training System" and filed Nov. 30, 2005, which claims priority to U.S. Provisional Patent Application No. 60/631,488, entitled Multimodal Emergency Medical Procedural Training Platform and filed Nov. 30, 2004. Each of those applications is incorporated here by this reference.

Application Ser. No. 13/481,725 also claims the benefit of U.S. Provisional Application Ser. No. 61/491,126 filed May 27, 2011 for Data Acquisition, Reconstruction, and Simulation; U.S. Provisional Application Ser. No. 61/491,131 filed May 27, 2011 for Data Validator; U.S. Provisional Application Ser. No. 61/491,134 filed May 27, 2011 for Peripheral Probe with Six Degrees of Freedom Plus 1; U.S. Provisional Application Ser. No. 61/491,135 filed May 27, 2011 for Patient-Specific Advanced Ultrasound Image Reconstruction Algorithms; and U.S. Provisional Application Ser. No. 61/491,138 filed May 27, 2011 for System and Method for Improving Acquired Ultrasound-Image Review. Each of those applications is incorporated here by this reference.

TECHNICAL FIELD

This invention relates to ultrasound probes, ultrasound probe systems, and ultrasound probe training systems.

BACKGROUND ART

Medical ultrasound hardware utilizes a mechanical transducer to broadcast high-frequency acoustic waves through the human body and then measure the reflection as a means for imaging. To use ultrasound imaging in the clinical setting, ultrasound operators must follow a strict convention to ensure that the image is oriented appropriately and the underlying anatomy is diagnosed correctly. By convention, the transducer is marked with a protruding indicator that must be oriented towards a patient's head or anatomic-right side during scanning. To aid guidance, a matching probe indicator icon is displayed on the screen of the ultrasound machine as a reference (generally on the left side of the screen). Maintaining this strict orientation takes on added significance when performing image-guided interventions (e.g., needle insertion), which may result in catastrophic implications if not performed correctly. For instance, a common pitfall, especially for novice users, is to inadvertently reverse the indicator default setting and erroneously orient the transducer as they are performing an incorrectly oriented, image-guided medical intervention.

However, by embedding motion-sensing technology directly within the housing of the ultrasound transducer (ultrasound probe), the position and orientation of the device can be tracked in relation to an indicator mark on the ultrasound screen in an automated manner, allowing assisting technologies to mitigate human error that arises from misalignment of the transducer indicator. As an example, motion sensors can be used to detect misalignment and provide visual or auditory alerts to notify the user about the probe indicator alignment (e.g., a probe indicator icon moves along the ultrasound screen in relation to the actual probe's orientation relative to a patient's body-rather than a preset position).

Furthermore, motion sensing hardware is employed by commercial solutions that provide real-time or just-in-time refresher training of ultrasound skills in a simulated environment. These simulators employ a motion-controlled handheld device in the shape of an ultrasound probe to recreate the experience of using a real device on a wide selection of pre-recorded patient cases with or without serious clinical pathologies. However, these simulators are currently only available as dedicated workstations or software packages for personal computers (PCs) and require an ad hoc external handheld motion sensing peripheral device for control. As a result, it is not possible to currently integrate the benefits of ultrasound training simulators within a real ultrasound device. The addition of an embedded motion sensor directly inside an ultrasound transducer will make this possible.

Having motion-sensing technology embedded directly within the housing of an ultrasound transducer will enable ultrasound devices to operate in two separate modes: a standard mode that allows the user to scan real patients using the traditional physics of ultrasound as is done currently, and a training mode that will instead allow the user to employ the same ultrasound probe as a motion sensing peripheral to navigate a multitude of existing patient cases augmented with annotations that help the operator expand and refine his or her knowledge of ultrasound imaging.

A typical handheld motion sensor utilizes various sensing components to measure displacement and orientation in three-dimensional (3D) space. While many technologies exist for tracking motion in space, inertial solutions allow the sensor package to retain a small form factor and work without needing additional external components to act as a fixed point of reference. Most inertial solutions combine accelerometers, gyroscopes, and a magnetometer in a single package to measure inertial motion and relate the orientation of the device with respect to the gravity vector and the earth's magnetic field. Whereas it has been previously proposed that this technology reside in a plastic casing of its own, it is now proposed that the electronic hardware be embedded and integrated within the plastic housing of current medical ultrasound transducers.

Also, to improve the fidelity of the simulation in training mode, an additional sensor (a "6+1 DOF" sensor) may be added to the embedded package for measuring compression, allowing the user to investigate the elastic properties of the underlying anatomy in the simulated environment by pressing the tip of the device against a surface with varying amounts of force.

DISCLOSURE OF INVENTION

Accordingly, the present invention can be described generally as an ultrasound system that includes an ultrasound machine and an ultrasound probe. The ultrasound machine displays an ultrasound image, and the ultrasound probe communicates with the ultrasound machine. The ultrasound probe includes an ultrasound transducer, ultrasound circuitry, a six degree of freedom (6-DOF) sensor, and a probe housing. The probe housing encases the ultrasound transducer and the 6-DOF sensor.

The ultrasound transducer transmits acoustic waves and measures the reflected waves to produce a reflected wave signal. The ultrasound circuitry receives the reflected wave signal from the ultrasound transducer and transmits an image signal to the ultrasound machine. The 6-DOF sensor measures the position and orientation of the ultrasound probe. Accordingly, the position and the orientation of the ultrasound probe may be tracked.

BEST MODE FOR CARRYING OUT THE INVENTION

Figure 1:
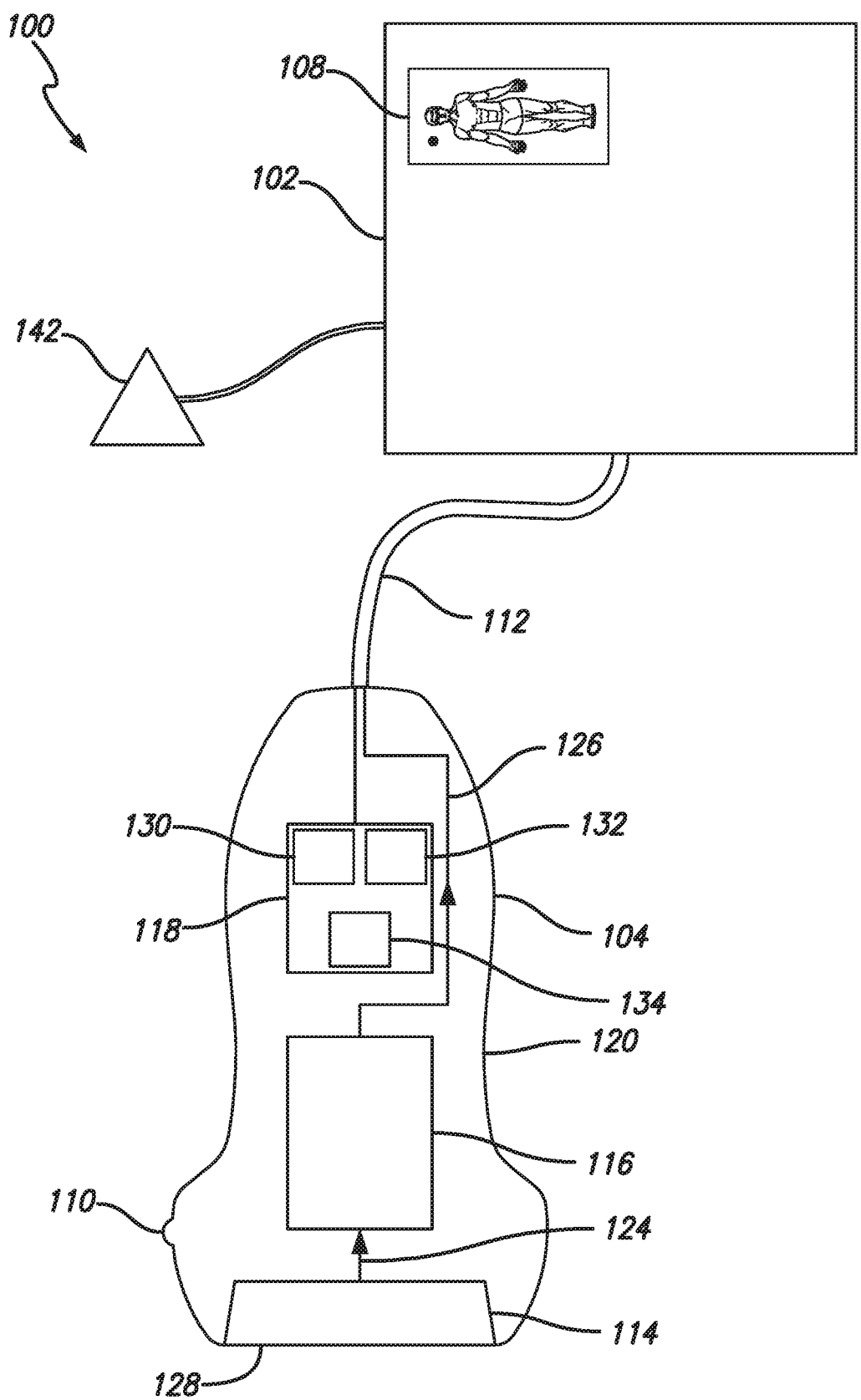
FIG. 1 is a schematic of an embodiment of the disclosed ultrasound system.
Figure 2:
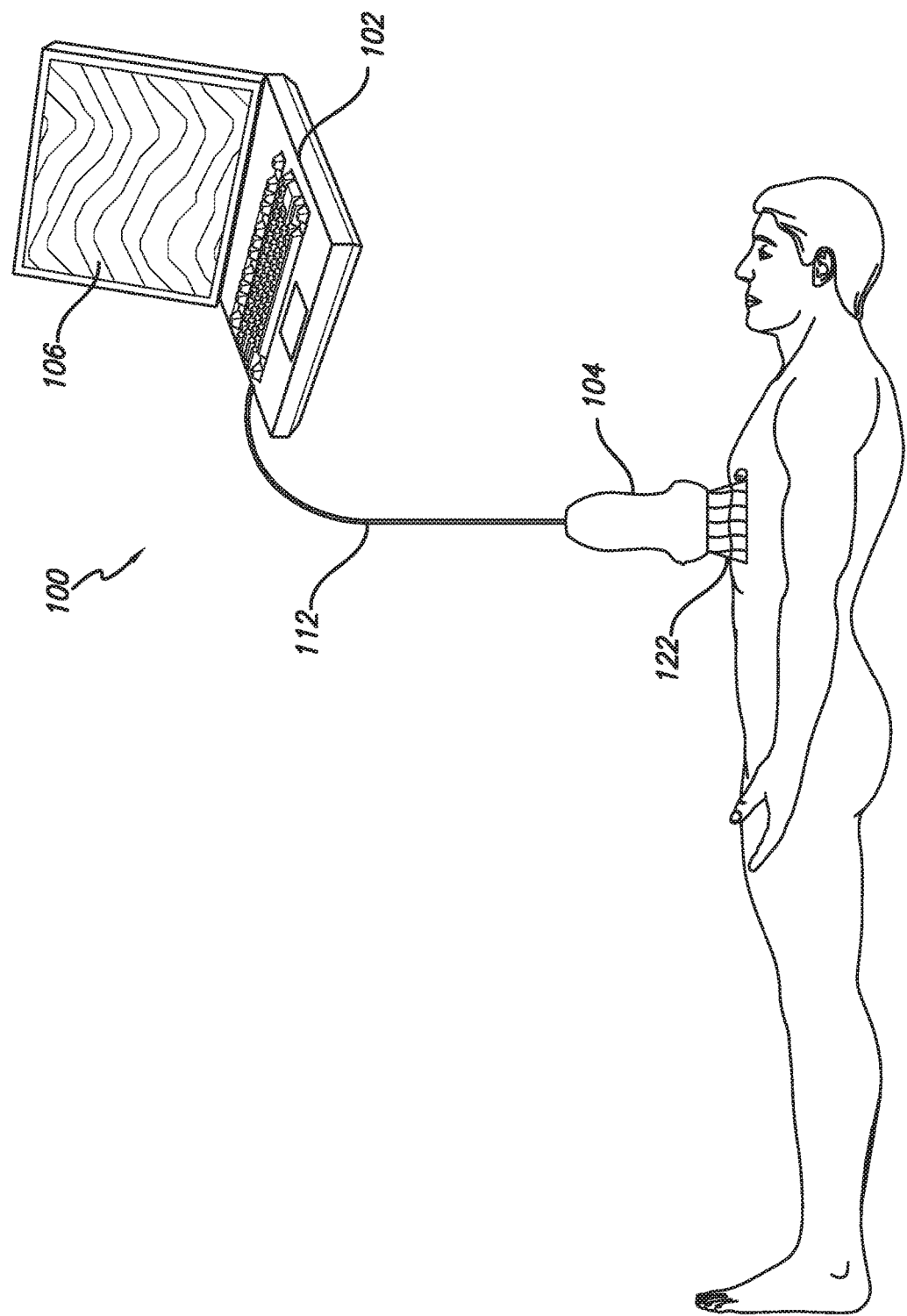
FIG. 2 is a schematic of an embodiment of the disclosed ultrasound system shown in standard mode, where the ultrasound probe is used to scan a real patient.
Figure 3:
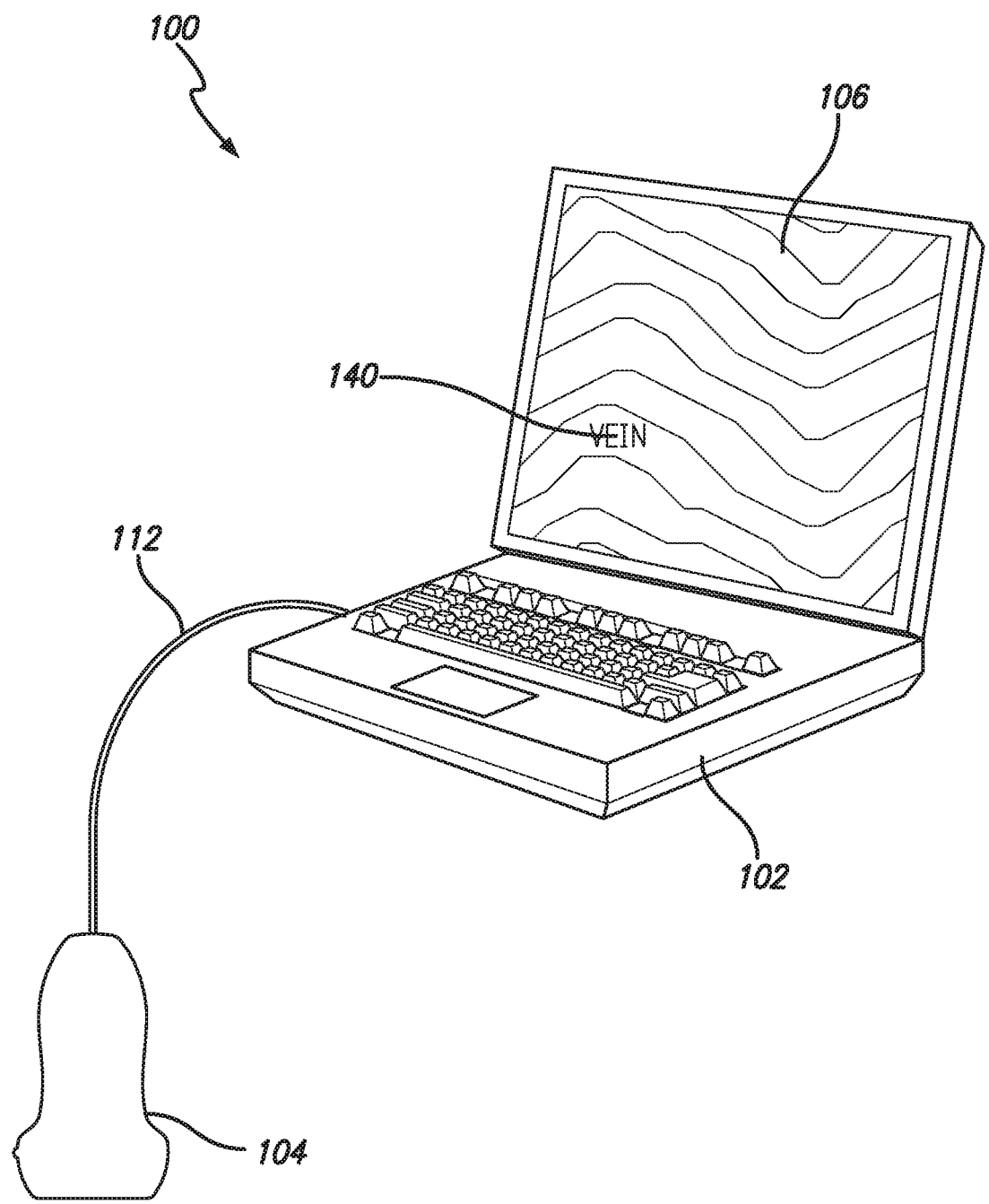
FIG. 3 is a schematic of an embodiment of the disclosed ultrasound system shown in training mode, where the same ultrasound probe as shown in FIG. 2 is now used as a motion sensing peripheral to navigate existing patient cases.
Figure 4:
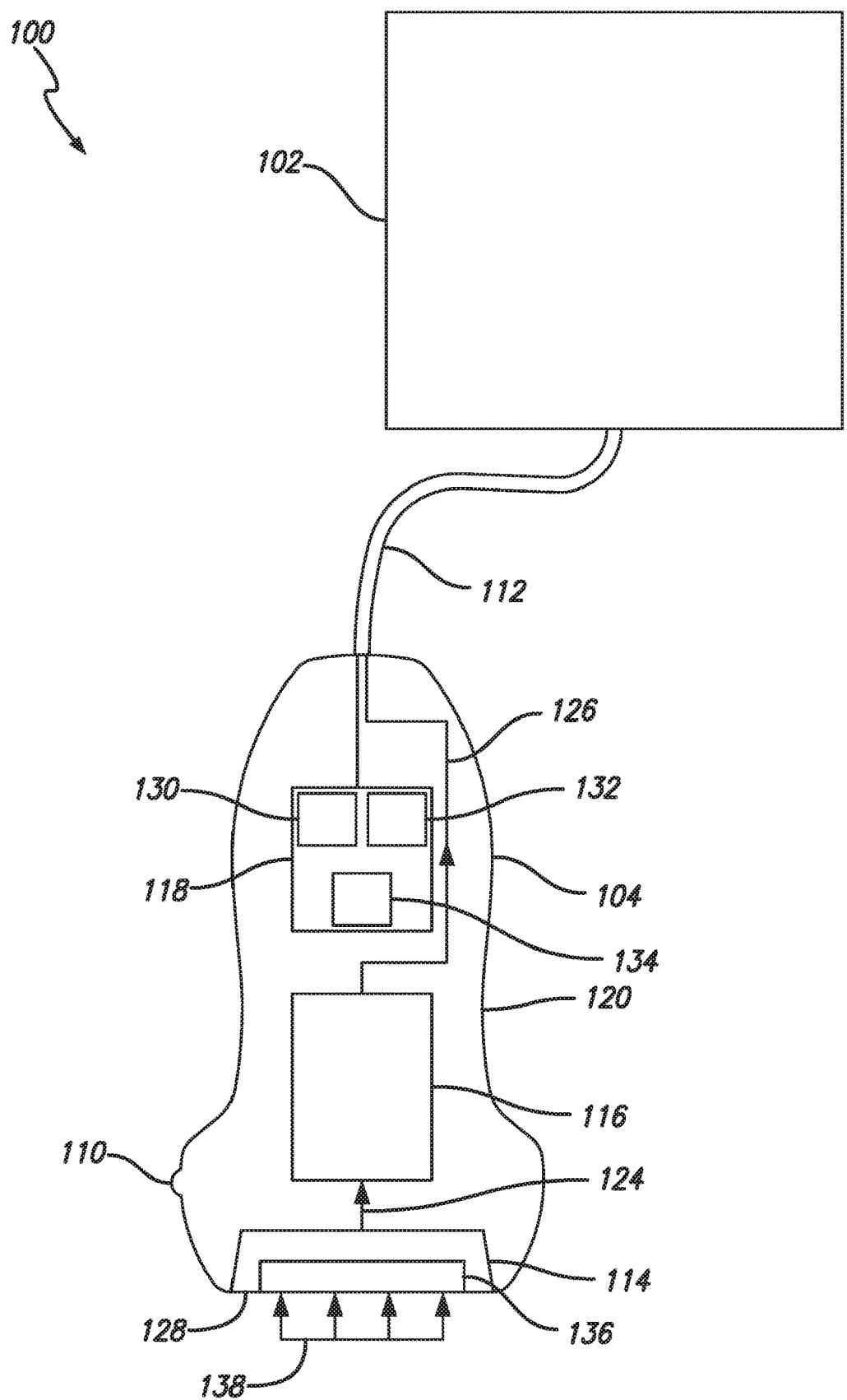
FIG. 4 is a schematic of an embodiment of the disclosed ultrasound system that includes a compression sensor.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

The ultrasound system 100 includes an ultrasound machine 102 and an ultrasound probe 104. The ultrasound machine 102 displays an ultrasound image 106. In a version of the invention, the image displayed by the ultrasound machine 102 includes a probe indicator icon 108. In another embodiment, the ultrasound probe 104 also includes a reference indicator 110, which is a direction indicator to orient the ultrasound probe 104.

The ultrasound probe 104 communicates with the ultrasound machine 102. In a version of the invention, the ultrasound probe 104 communicates with the ultrasound machine 102 through a data cable 112. In other versions, the communication is wireless.

The ultrasound probe 104 includes an ultrasound transducer 114, ultrasound circuitry 116, a six degree of freedom (6-DOF) sensor 118, and a probe housing 120. The probe housing 120 encases the ultrasound transducer 114 and the 6-DOF sensor 118.

The ultrasound transducer 114 transmits acoustic waves 122 and measures the reflected acoustic waves 122 to produce a reflected wave signal 124. The ultrasound circuitry 116 receives the reflected wave signal 124 from the ultrasound transducer 114 and transmits an image signal 126 to the ultrasound machine 102. The 6-DOF sensor 118 measures the position and orientation of the ultrasound probe 104.

Preferably, the 6-DOF sensor 118 is an inertial sensor. In an embodiment, the 6-DOF sensor 118 includes an accelerometer 130, a gyroscope 132, and a magnetometer 134. The 6-DOF sensor 118 can be used to detect misalignment and provide a visual alert (for example, in conjunction with the probe indicator icon 108) or an auditory alert to the user about the reference indicator 110 alignment.

In a version of the invention, the ultrasound probe 104 also includes a sensing head 128 at which the ultrasound transducer 114 transmits acoustic waves 122 and measures reflected waves.

In a preferred version, the ultrasound probe 104 also includes a compression sensor 136 that measures the force 138 applied to the sensing head 128. In that version, the probe housing 120 also encases the compression sensor 136. The compression sensor 136 allows the user to investigate the elastic properties of the underlying anatomy in the simulated environment by pressing the tip of the device (for example, the sensing head 128) against a surface with varying amounts of force 138. Preferably, the compression sensor 136 is a resistive strain gauge or other mechanical means that will not interfere with the operation of the ultrasound transducer 114. If the compression sensor 136 interferes with the operation of the ultrasound transducer 114, in some versions the compression sensor 136 may be disabled mechanically when the ultrasound system 100 is operated in the standard mode. In an alternative embodiment, the ultrasound transducer 114 (which is typically built using a highly sensitive piezoelectric element) can itself be used to measure compression directly without a separate compression sensor 136.

With motion-sensing technology embedded directly within the probe housing 120, the ultrasound system 100 can operate in two separate modes: a standard mode that allows the user to use the ultrasound probe 104 to scan real patients using the traditional physics of ultrasound as is done currently, and a training mode that will instead allow the user to employ the same ultrasound probe 104 as a motion sensing peripheral to navigate existing patient cases, perhaps augmented with annotations 140 that help the operator expand and refine his or her knowledge of ultrasound imaging.

More specifically, an ultrasound system 100 equipped with this novel kind of ultrasound probe 104 allows the machine to provide an additional mode of operation for training (training mode). When the training mode is enabled, the user can move the ultrasound probe 104 on the patient's body, a medical mannequin, or other arbitrary surface to navigate a pre-recorded patient case. The software loaded on the ultrasound machine 102 will respond to the motion of the ultrasound transducer 114 in a simulated environment in the same manner as when operating the ultrasound machine 102 in traditional mode (standard mode) with the real physics of ultrasound. The added benefit of the training mode is that the ultrasound operator can correlate what is observed in the real patient with a large library of pre-recorded real and simulated ultrasound cases that may exhibit a wide range of known pathologies. Furthermore, pre-recorded real and simulated ultrasound data may be augmented with additional anatomical annotations 140 that provide further insight on the details of how to use ultrasound imaging in the clinical setting. Those anatomical annotations 140 may include the labeling of pathologies or anatomical structures that are visible in the ultrasound data.

Accordingly, the disclosed solution can mitigate human error that arises from misalignment of the transducer's reference indicator 110 thorough manual and automatic misalignment detection.

Manual misalignment detection—The ultrasound operator can validate the appearance of a desired anatomical region with a pre-recorded case and verify that he or she oriented the ultrasound probe 104 correctly when scanning a patient. This approach does not need any additional equipment or modification beyond the disclosed embedded motion sensor.

More specifically, to calibrate the system, the user places the ultrasound probe 104 at a known position with respect to the ultrasound machine 102. This is necessary to track the position of the ultrasound probe 104 with respect to the ultrasound machine 102 without the aid of any additional sensor or technology. The ultrasound machine 102 provides the user with an on-screen visual reference to establish how the sensor should be aligned (for example, with the probe indicator icon 108). All existing ultrasound machines provide such reference in the form of a small colored circle on the side of the screen. For the disclosed application it may be also useful, but not necessary, to show a visual representation of the patient's body on-screen to provide additional guidance.

The ultrasound operator may then scan the patient's body, a medical mannequin, or other arbitrary surface. The embedded 6-DOF sensor 118 informs the ultrasound machine 102 about the position of the 6-DOF sensor 118 throughout the scanning session.

Software in the ultrasound machine 102 continuously monitors the position and orientation of the ultrasound probe 104 during the scanning session using the readings from the 6-DOF sensor 118. The calibration procedure noted above allows the software to compute the relative position of the 6-DOF sensor 118 with respect to the ultrasound machine 102. If the software detects that the ultrasound probe 104 is not aligned correctly according to established medical conventions, then a visual or audio alert is generated to inform the operator about the hazard.

Automatic misalignment detection—If additional means (as explained below) are available for determining the position of the ultrasound unit with respect to the ultrasound transducer 114, software on the device can determine automatically whether or not the current orientation of the ultrasound transducer 114 is correct by checking if the expected medical conventions are being honored. This solution does not require a separate calibration step, and it may be more accurate over the extent of the scanning session.

More specifically, this approach requires two-point motion sensing solution where a reference beacon 142 is placed at fixed position on the ultrasound machine 102 and the receiver is placed inside the ultrasound probe, preferably as part of the 6-DOF sensor 118. During the ultrasound scanning process, the two-point sensor solution informs the ultrasound machine 102 about the position of the 6-DOF sensor 118 relative to the ultrasound machine 102 throughout the scanning session. Software on the ultrasound machine 102 continuously monitors the position and orientation of the ultrasound probe 104 with respect to the ultrasound machine 102 during the scanning session using the readings from the two-point sensor solution (that is, the reference beacon 142 in conjunction with the 6-DOF sensor 118). If the software detects that the ultrasound probe 104 is not aligned correctly according to established medical conventions, then a visual or audio alert is generated to inform the operator about the hazard.

While the present invention has been described with regards to particular embodiments, it is recognized that additional variations of the present invention may be devised without departing from the inventive concept.

INDUSTRIAL APPLICABILITY

This invention may be industrially applied to the development, manufacture, and use of ultrasound probes, ultrasound probe systems, and ultrasound probe training systems.

What is claimed is:

1. An embedded ultrasound training system, the ultrasound training system having a standard mode and a training mode, the ultrasound training system comprising:
    (a) an ultrasound machine configured to operate in the standard mode and the training mode;
    (b) an ultrasound probe operatively connected to the ultrasound machine, the ultrasound probe comprising:
        (i) a sensing head;
        (ii) an ultrasound transducer that, when operated, transmits acoustic waves from and measures reflected waves received at the sensing head to produce a reflected wave signal,
        (iii) ultrasound circuitry, the ultrasound circuitry receiving the reflected wave signal from the ultrasound transducer and transmitting an image signal to the ultrasound machine,
        (iv) an inertial sensor configured for measuring a position and an orientation of the ultrasound probe, the inertial sensor comprising an accelerometer;
        (v) a compression sensor, the compression sensor comprising a resistive strain gauge and measuring a force on the sensing head, and
        (vi) a probe housing encasing the ultrasound transducer, the inertial sensor, and the compression sensor; and
    (c) a library of pre-recorded ultrasound cases connected to the training mode to simulate the functioning of the ultrasound probe as if in the standard mode, wherein when the ultrasound transducer is active in the standard mode, a user can scan a patient through transmitted acoustic waves and reflected waves, and wherein when the ultrasound transducer is inactive in the training mode, the ultrasound probe functions as a motion sensing peripheral in a simulated environment to navigate the library of prerecorded ultrasound cases, whereby, the position and the orientation of the ultrasound probe are displayed on the ultrasound machine.

2. The ultrasound system of claim 1, where the ultrasound transducer is a piezoelectric element.

3. An ultrasound system, comprising:
    (a) an ultrasound machine configured to operate in a standard mode and a training mode; and
    (b) an ultrasound probe operatively connected to the ultrasound machine, the ultrasound probe comprising:
        (i) an ultrasound transducer that, when operated, transmits acoustic waves and measures reflected waves to produce a reflected wave signal,
        (ii) ultrasound circuitry, for receiving the reflected wave signal from the ultrasound transducer and for transmitting an image signal to the ultrasound machine,
        (iii) a motion sensor configured for measuring a position and an orientation of the ultrasound probe, and
        (iv) a probe housing encasing the ultrasound transducer and the motion sensor, wherein when the ultrasound transducer is active in the standard mode, a user can scan a patient through the acoustic waves and the reflected waves, wherein when the ultrasound transducer is inactive in the training mode, the user can use the ultrasound probe as a motion sensing peripheral.

4. The ultrasound system of claim 3, further comprising a library of pre-recorded ultrasound cases connected to the training mode to simulate the functioning of the ultrasound probe as if in the standard mode.

5. The ultrasound system of claim 3, where the ultrasound probe further includes a reference indicator, the reference indicator comprising a direction indicator to orient the ultrasound probe.

6. The ultrasound system of claim 3, where the ultrasound probe further includes a sensing head at which the ultrasound transducer transmits the acoustic waves and measures the reflected waves.

7. The ultrasound system of claim 6, where the ultrasound transducer also configured to measure a force on the sensor head.

8. The ultrasound system of claim 7, where the ultrasound transducer is a piezoelectric element.

9. The ultrasound system of claim 3, where the motion sensor is an inertial sensor.

10. The ultrasound system of claim 3, where the motion sensor comprises an accelerometer.

11. The ultrasound system of claim 3, where the ultrasound probe further comprises a compression sensor that measures a force on the ultrasound probe, and the probe housing also encases the compression sensor.

12. The ultrasound system of claim 11, where the compression sensor comprises a resistive strain gauge.

13. A method, comprising the steps of:
(a) providing the ultrasound training system of claim 1; and
(b) using the ultrasound training system in the standard mode by:
  (i) activating the ultrasound transducer,
  (ii) operating the ultrasound probe to scan the patient, the ultrasound transducer transmitting the acoustic waves and the reflected waves to produce the reflected wave signal,
  (iii) the ultrasound circuitry receiving the reflected wave signal from the ultrasound transducer and transmitting the image signal to the ultrasound machine, and
  (iv) the ultrasound machine displaying an ultrasound image.

14. The method of claim 13, further comprising using the ultrasound training system in the training mode by first enabling the training mode, measuring a position and orientation of the ultrasound probe, and employing the ultrasound probe as a motion sensing peripheral to navigate the library of pre-recorded ultrasound cases based on the measured position and orientation of the ultrasound probe.

15. The method of claim 14, where the step of using the ultrasound training system in the training mode further comprises coordinating a probe indicator icon to the inertial sensor such that the probe indicator icon moves in a coordinated fashion to a reference indicator of the ultrasound probe, and the library of pre-recorded ultrasound cases responds to the measured position and orientation of the ultrasound probe.

16. The method of claim 15, where the step of coordinating the probe indicator icon in relation to the inertial sensor comprises wirelessly coupling the inertial sensor to a reference beacon connected to the ultrasound training system.

17. The method of claim 15, further comprising the steps of:
(a) detecting a misalignment between the probe indicator icon and the reference indicator; and
(b) providing an alert to a user about the detected misalignment.

18. The method of claim 17, where the alert is visual.

19. The method of claim 17, where the alert is auditory.

20. The method of claim 14, where the step of using the ultrasound training system in the training mode further comprises the step of augmenting the library of pre-recorded ultrasound cases with one or more anatomical annotations before navigating the library of pre-recorded ultrasound cases.

\* \* \* \* \*